(12) United States Patent
Ciezki et al.

(10) Patent No.: US 6,494,835 B1
(45) Date of Patent: Dec. 17, 2002

(54) METHOD AND APPARATUS FOR INTRAVASCULAR BRACHYTHERAPY TREATMENT PLANNING

(75) Inventors: Jay P. Ciezki, Shaker Heights, OH (US); Urs Hafeli, Cleveland, OH (US); David Bleam, Orangevale, CA (US)

(73) Assignees: Jomed Inc., Rancho Cordova, CA (US); Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/505,388

(22) Filed: Feb. 16, 2000

(51) Int. Cl.[7] .................................................. A61B 8/00
(52) U.S. Cl. ...................................................... 600/439
(58) Field of Search ................................. 600/443, 459, 600/461, 467, 468, 6, 3, 7, 439

(56) References Cited

U.S. PATENT DOCUMENTS

| | | | | |
|---|---|---|---|---|
| 5,651,366 A | * | 7/1997 | Liang et al. | 600/461 |
| 5,840,008 A | * | 11/1998 | Klien et al. | 600/3 |
| 5,882,291 A | * | 3/1999 | Bradshaw et al. | 600/3 |
| 6,077,213 A | * | 6/2000 | Ciezki et al. | 600/3 |

* cited by examiner

*Primary Examiner*—Francis J. Jaworski
*Assistant Examiner*—Maulin Patel
(74) *Attorney, Agent, or Firm*—Leydig, Voit & Mayer, Ltd.

(57) ABSTRACT

A method for providing intravascular brachytherapy includes the step of positioning a radiation source within a target area to be radiation and orienting the attenuator found on the catheter. Once the attenuator or shield is properly oriented, a reference or normalization point or marker (508) is selected. This reference marker (508) can placed, as one example, on the external elastic lamina closest to catheter (100) and can serve as a reference point for the brachytherapy treatment. Several other points of interest can be is selected (504, 506, 510) on the image (500) or images that have been gathered of the treatment site, with dosage levels (512, 522, 520 and 518) being display automatically on the display (406) close to the IVUS image (500).

13 Claims, 5 Drawing Sheets

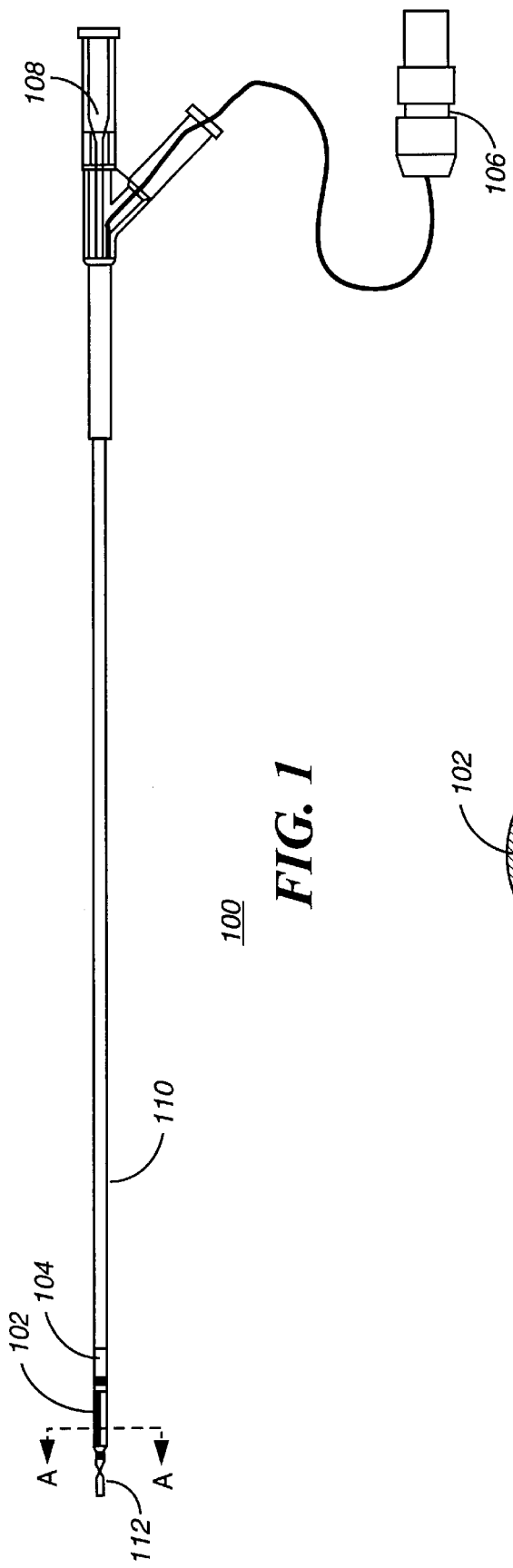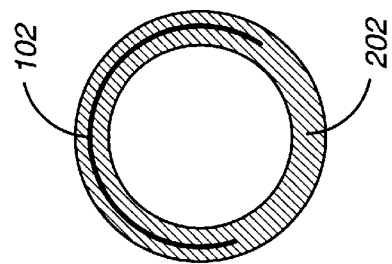

//METHOD AND APPARATUS FOR INTRAVASCULAR BRACHYTHERAPY TREATMENT PLANNING

TECHNICAL FIELD

This invention relates in general to the field of intravascular brachytherapy, and more particularly, to a method and apparatus for providing intravascular bracytherapy treatment planning.

BACKGROUND

Research has found that up to 45% of the angioplasty procedures performed require an additional intravascular intervention procedure be performed after several months due to restenosis. These additional interventions do not only increase the cost of health care, but also have serious effects on the health and well being of patients having to undergo these additional medical procedures.

Many recent medical studies have demonstrated that intravascular radiation treatment, also known as intravascular brachytherapy, may inhibit restenosis in vessels that have undergone angioplasty or other coronary revascularization procedures (e.g., atherectomy, ablations, etc.). This is a welcome sign for patients who have undergone angioplasty or other revascularization procedures, given that brachytherapy may avoid patients from having to undergo subsequent procedures.

One problem that currently occurs during intravascular brachytherapy procedures is that physicians have to spend a large amount of time prior to, and/or during a procedure in treatment planning in order to determine how much radiation dosage to apply and where to apply the dosage within the treatment site. Since undertreating with radiation can result in not inhibiting the neointima and, in some cases, can actually result in stimulating smooth muscle cell proliferation and extra-cellular matrix production. While overtreating with radiation can induce necrosis or aneurysm. Given this, physicians are very cautious and take time in developing a proper radiation treatment plan for patients.

Current brachytherapy systems, even those that employ IVUS guidance tend not to provide physicians with the needed features and information needed to form a proper treatment plan, much less one that takes a minimal amount of time. A need thus exists in the art for a method and apparatus that can provide a solution to this problem.

BRIEF DESCRIPTION OF THE DRAWINGS

The features of the present invention, which are believed to be novel, are set forth with particularity in the appended claims. The invention, together with further objects and advantages thereof, may best be understood by reference to the following description, taken in conjunction with the accompanying drawings, in the several figures of which like reference numerals identify like elements, and in which:

FIG. 1 shows a directional radiation delivery catheter that can be used with the present invention.

FIG. 2 shows a cross-sectional view of the radiation delivery catheter of FIG. 1 taken along line A—A.

DETAILED DESCRIPTION OF THE PREFERRED EMBODIMENT

Figure 3:
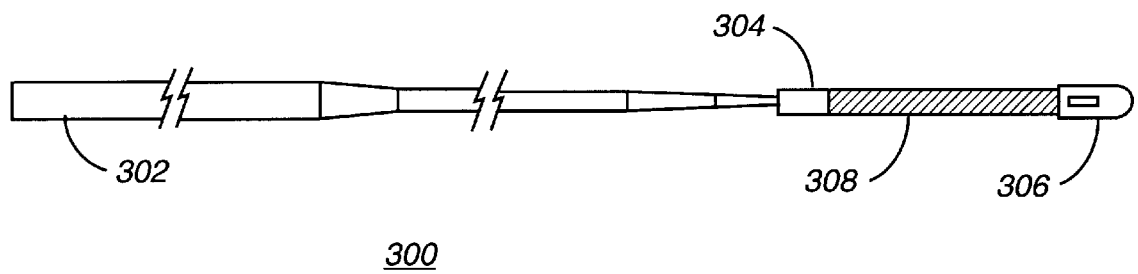
FIG. 3 shows a radiation source wire that can be inserted into the radiation delivery catheter of FIG. 1.

While the specification concludes with claims defining the features of the invention that are regarded as novel, it is believed that the invention will be better understood from a consideration of the following description in conjunction with the drawing figures, in which like reference numerals are carried forward.

Referring now to FIG. 1, there is shown a directional radiation delivery catheter having IVUS guidance 100 for use with the present invention. Although a directional radiation delivery catheter is preferred, the present invention can be carried out with any type of radiation delivery device. Catheter 100 includes a catheter shaft 110, an IVUS transducer assembly 104 mounted on the shaft and a directional radiation shield 102 located at the distal end of the catheter. A radiation lumen 108 extends along the majority of the catheter's length. An electrical connector 106 interconnects the IVUS transducer assembly 104 to an IVUS system (shown in FIG. 4). At the distal end of catheter 100 is a swivel tip 112 having a guide wire lumen. The swivel tip 112 minimizes torquing of the catheter 100 during movement of the catheter through tight vessel bends. The preferred directional radiation delivery catheter 100 is described in a U.S. patent application entitled "An Intravascular Radiation Delivery Device", having Ser. No. 08/827,489 and filed on Mar. 28, 1997, to Ciezki, et al. which is hereby incorporated by reference as if fully set forth herein.

Radiation delivery catheter 100 includes a shield or attenuator section 102 shown in cross section in FIG. 2. Shield 102 is provided along a predefined length (e.g., 25 millimeters) and is wrapped around a portion of the catheter (e.g., about 235 degrees around the catheter). The shield 102 can comprise a piece of gold foil located within the catheter body. A window or non-shielded portion 202 (e.g., 125 degrees) allows for the radiation to be directed or focused as explained in detail in the above noted patent application.

In FIG. 3 there is shown a radiation source wire 300 that can be inserted into the catheter lumen 108, the radiation source wire 300 is fed into catheter 100 until radiation coil 308 reaches the radiation delivery area located at the distal end of the catheter close to shield 102. Source wire 300 includes a tapered core wire 302 and a source tip 306. A radiopague source band 304 allows an IVUS system operator to determine that the source wire has been properly inserted into catheter 100. A radiation source coil 308 preferably formed from Rhenium or Tungsten is activated with radiation as is known in the art.

Figure 4:
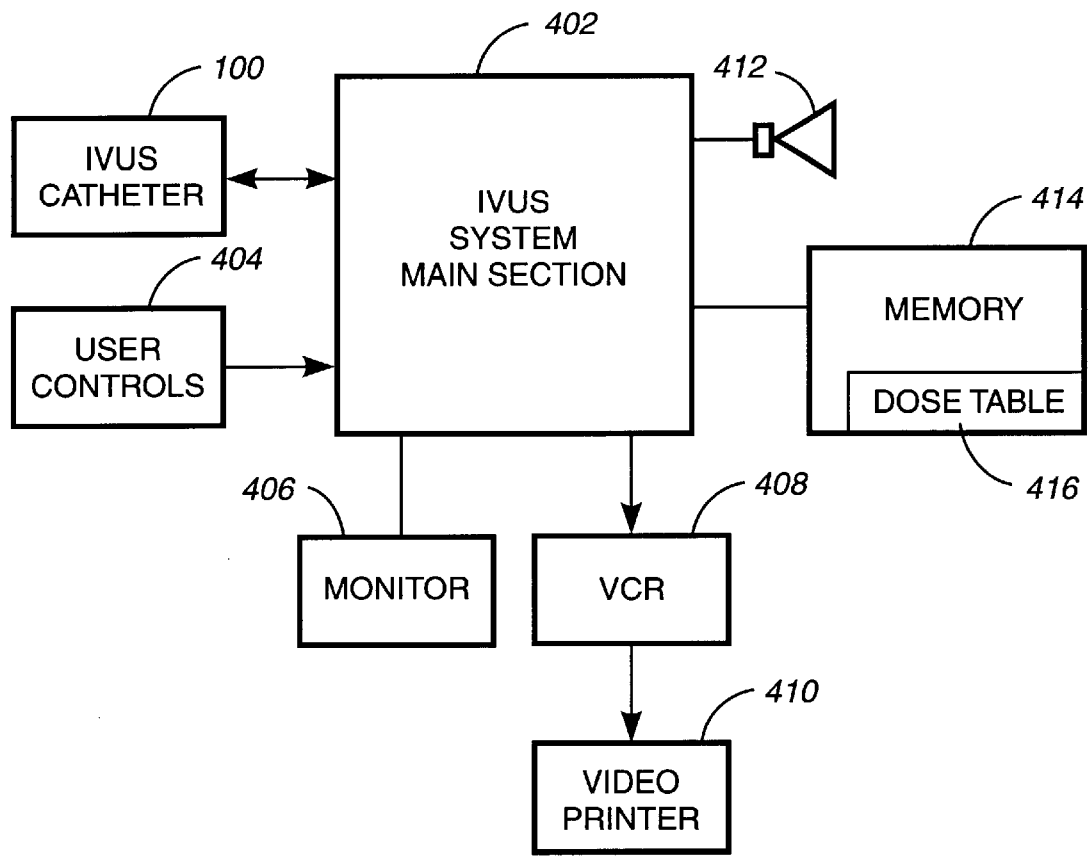
FIG. 4 shows a simplified block diagram of an intravascular ultrasound (IVUS) system in accordance with the present invention.

Referring now to FIG. 4, there is shown a simplified block diagram of an IVUS system 400 in accordance with the present invention. IVUS system 400 preferably comprises an IN-VISION™ intravascular ultrasound system manufactured by EndoSonics Corporation of Rancho Cordova, Calif., although other IVUS system can be used. The IVUS catheter 100 is coupled to the main section 402 of the IVUS system that processes the incoming ultrasound information and presents it to the user via display 406. The main section 402 includes the analog-to-digital (ADC) section, beam former, digital vector processor, scan converter and reconstruction controller as known in the art. The recovered images can be displayed in display monitor 406 or stored in video recorder (VCR) 408 and/or printed using printer 410.

A set of user controls 404 such as a keyboard and track ball or mouse, allow the system operator to enter information and control the operations of system 400. A speaker 412 is also provided in order to provide audible alerts to the system operator. A memory section 414 which can include random access memory (RAM), read-only memory (ROM) and a hard drive or other forms of storage space helps store the radiation dose table 416 which includes information on the dose profile for the radiation source wire 300. The dose profile information stored in the radiation dose table 416 takes into account the attenuation affects of shield 102. The dose table is preferably an empirical table statistically collected from a number of actual radiation catheters. Alternatively, the table can be generated using a software simulation program which can simulate the radiation pattern of the radiation source that is going to be applied to the patient (e.g., 100 mCi $^{188}$W/$^{188}$Re radiation source). The dose table contains dose rates in Grays/minute (Gy/min.) and takes into account the shield found in catheter 100. The dose table 416 will have as one example, 160 rows and columns, with the point at Row 81/Column 81 in the table relating to the center of the source wire on the IVUS image. The resolution for each point in the graph is about 0.1 millimeter. The numbers loaded on the table are for the radiation source right after being irradiated at time 0. The dose rates for example for a $^{188}$W radiation source which has a half-fife of 69.4 days, after a period of time "t" has elapsed in days, can be calculated as follows:

$$D_t = D_0 X \exp(-1\ n2^* t/69.4)$$

The invention will automatically adjust the dose rates for the particular source wire used, since the activation date of the source wire is entered into the IVUS system 400 as will be described further below.

Figure 5:
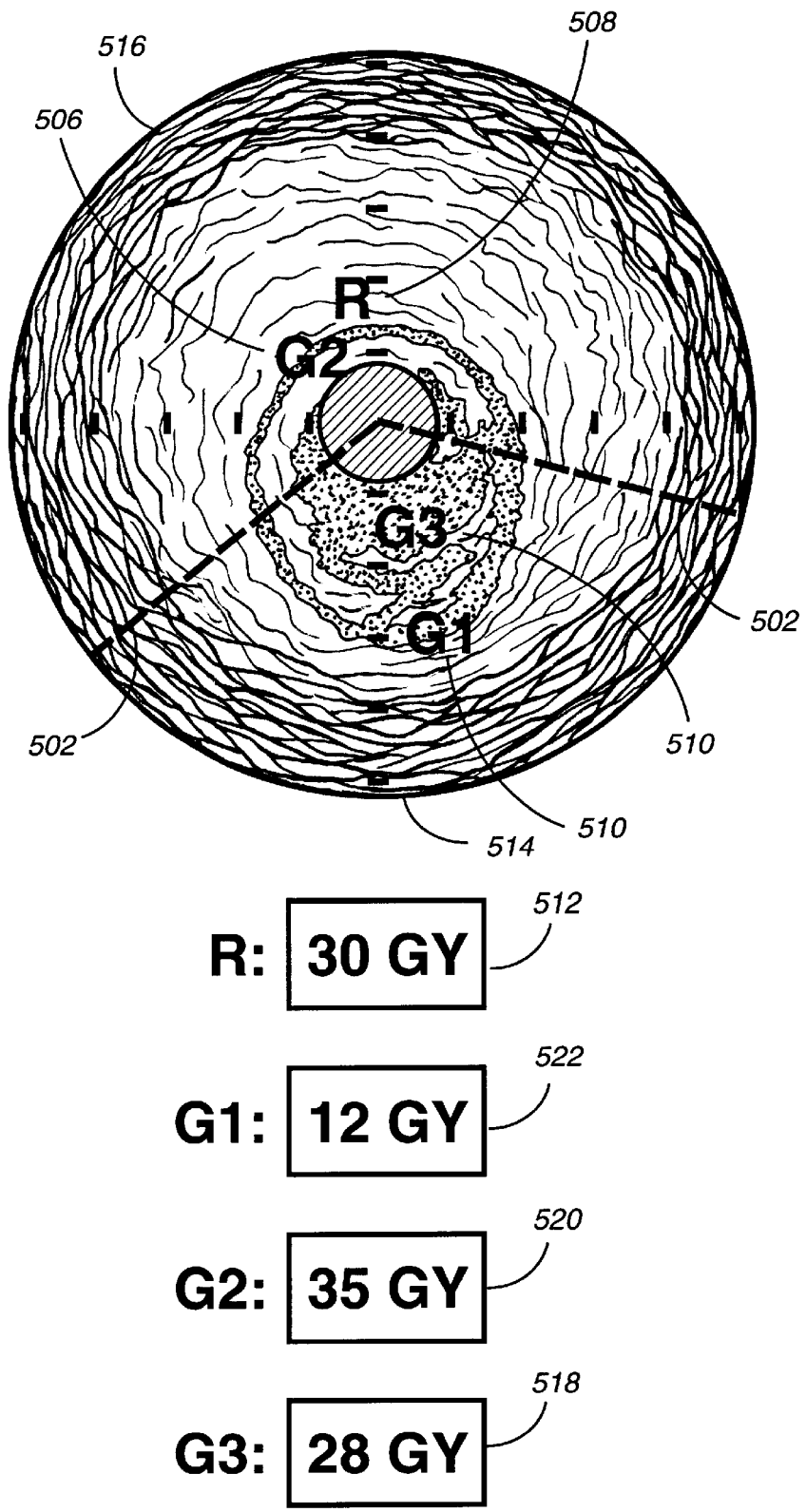
FIG. 5 shows an IVUS image along with makers used in accordance with the present invention.

Referring now to FIG. 5, there is shown an IVUS image collected by IVUS system 400 and displayed in monitor 406. In accordance with the preferred embodiment of the invention, the IVUS image collected is provided with two radiation shield marker lines 502 that indicate the boundaries of the unshielded area 514 of catheter 100 when the radiation boundaries are activated. The radiation shield maker lines 502 can be activated on the display by performing a command key sequence via the IVUS system keyboard. Marker lines 502 bound the window area 202 of the catheter and allow the attending physician to know where the shielded portion 516 and unshielded portion 514 of the directional catheter lie in relation to the gathered image.

The attending physician can then torque the catheter in order to adjust the IVUS image according to the stenosis that has been detected. The shielded portion 516 of the catheter will typically be torqued so that it is closest to the area of the lumen that is closest to the vessel wall. This allows the non-shielded or window portion 514 to be pointed or directed to the area of the vessel that has the most occlusion. Once the image is properly torqued, the physician enters the radiation measurement mode and selects a reference or normalization point dose level 508 (denoted as "R") on the image. This can be done by using the track ball or mouse which is part of user controls 404 which moves a on-screen cursor to a particular area on the image.

Figure 6:
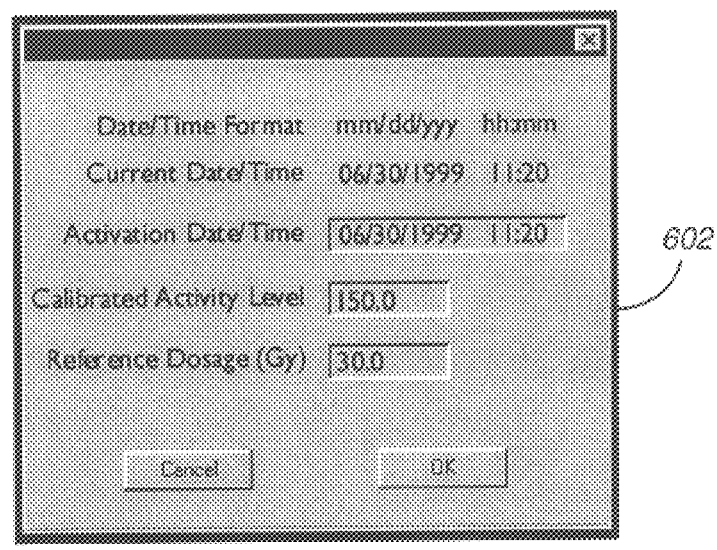
FIG. 6 shows a radiation source data entry screen in accordance with the present invention.
Figure 7:
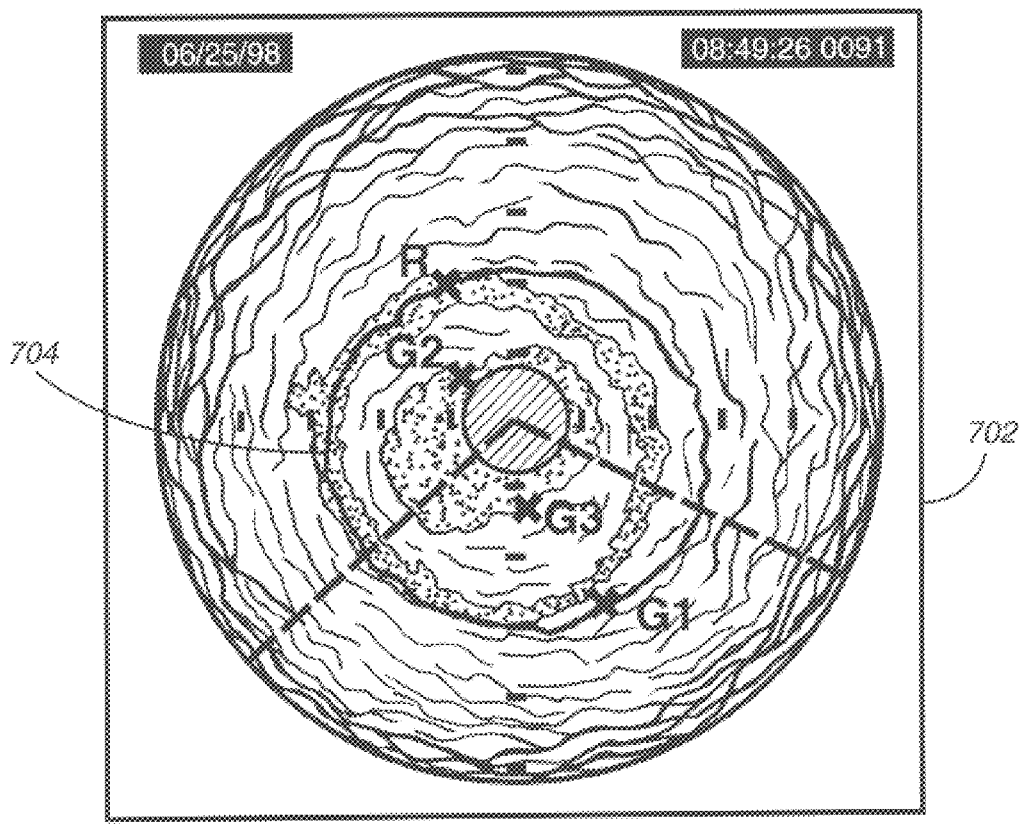
FIG. 7 shows an IVUS image having a reference radiation isodose curve in accordance with one embodiment of the present invention.

Prior to the marker "R" being displayed, a prompt window 602 as shown in FIG. 6 is displayed on monitor 406. The window prompts the physician to enter the activation date of the radiation source wire 300, the activity level of the wire and the dosage level at the reference point that is being selected. This helps to serve as a redundant check of the source delivery carton, which displays the activation date and activity level of the source wire 300. Alternatively, the date and time of creation of the source wire 300 can be stored in the catheter's EPROM, which is located within electrical connector 106. This assumes that the radiation delivery catheter is matched to a particular source wire 300. As a further alternative, the source wire can have the activation date, time and activation activity level stored in an EEPROM or bar code located on the wire which can be automatically read by IVUS system 400. The activation date and time information is used by IVUS system 400 to update the radiation dose information found in dose table 416.

A default reference dosage level for the reference point 508 is set to a default level of 30 Gray (Gy) in the system, which has been found to be an acceptable dosage level ceiling. Although the radiation dosage level at the reference point can be adjusted via widow 602. The physician will typically select an area on the vessel as shown in the image 500 that he wants to use as the dosage ceiling, in the example shown, it could be the external elastic lamina (EEL) nearest the catheter.

Once the information has been entered, the reference marker 508 appears on the image, along with the reference dosage level 512 at the selected reference point 508, in this case the monitor shows that marker "R" will be dosed at a level of 30 Gy. Once the proper dosage ceiling location or reference location 508 has been selected, the system allows the physician to select several other locations on the image 500 or on one of the other images collected (not shown) that he wants to monitor. These other areas are noted as "G1" 504, "G2" 506 and "G3" 508 can again be selected by the physician using the trackball or mouse that is part of the system and placing and activating the cursor in the selected locations.

Preferably, marker "G1" 504 is placed on the EEL located in the unshielded area 514 of image 500. The dosage at marker G1 504 is shown in box 522 that is displayed next to or close to the IVUS image. The software of the present invention allows a few other points of interest (e.g., the endothelium, etc.) to also be selected and highlighted. These other markers are shown as "G2" 506 and "G3" 508. Their corresponding dosage levels are shown in boxes 520 and 518. As shown, the present invention provides an attending physician with a quick way of setting a ceiling dosage level for a particular point on an image and also be able to track the dosage levels at a few other selected points of interest. The dose at any other point (e.g., "G1" 522, etc.) other than the normalization or reference point 508 can be calculated as follows:

"other point" dose level=(dose_rate_at_other_point*(30 Gy reference_level/dose_rate_at_reference point)).

In the preferred embodiment, the reference point marker 508 is fixed along all of the IVUS images that are collected for the particular treatment site, this saves time, but assumes that their has been minimal torquing of the catheter between images. This has been found to be the case when using the radiation delivery catheter 100 having the swivel guide wire lumen tip 112. Movement or replacement of the reference marker 508 automatically updates all calculations on all other images gathered for the target site.

In a further embodiment of the invention, one or more isodose curves 704 are added to the image that is displayed.

Preferably, the reference dosage curve for marker 508 is shown This isodose curve can be generated based on simulation files for the particular radiation source that will be applied (e.g., $^{188}$W/$^{188}$Re, etc.). These simulation files can be stored in memory section 414. This reference dosage level curve will help the physician visualize along what part of the image, the reference dosage level of 30 Gy will be applied.

Figure 8:
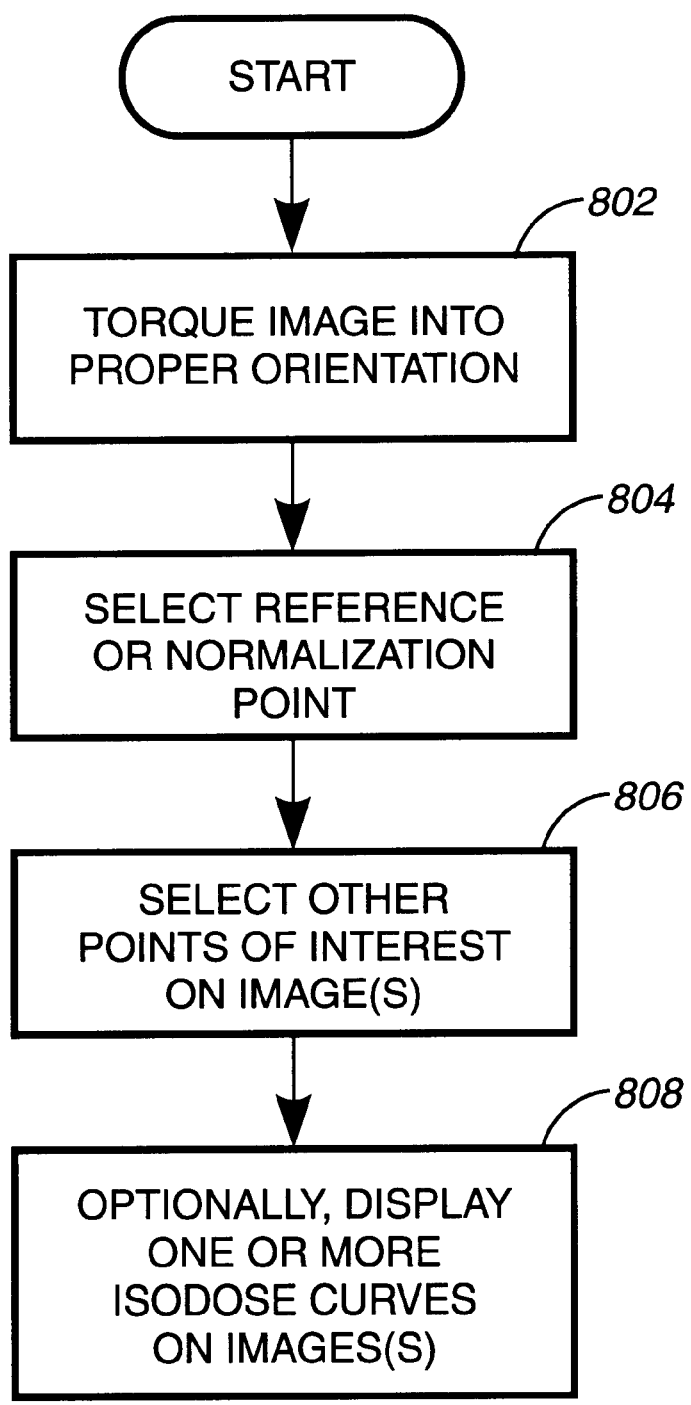
FIG. 8 shows a simplified flowchart highlighting the steps taken in accordance with the present invention.

In FIG. 8 there is shown a simplified flowchart highlighting the steps taken in accordance with the invention. In step 802, the image is torqued into proper orientation. In step 804, the reference or normalization point 508 is selected. At this time the physician also enters the activation date and time of the source wire 300 that will be used. This information as mentioned above is used to update the dosage rates found in dosage table 416 in order to account for the decay of the radiation source over time.

In step 806, several other points/markers 504, 506 and 510 are selected and placed on the IVUS image or images. These markers can be placed on the same IVUS image 500 or other images that have been collected of the targeted site. These other points allow a physician to see the dosage levels that will be applied to several points of interest at one time. The markers can be moved and the dosage rates 522, 520 and 518 associated with the markers can be immediately updated on the screen. Optionally, in step 808, one or more isodose curves, such as curve 704, can also be displayed over the IVUS image(s).

Once all of the markers have been inserted, the IVUS system will prompt the physician to insert the source wire 300 into the patient via the delivery catheter 100. The system will let him know how long to maintain the source wire placed in the patient in order to achieve the desired dosage levels previously selected. Once the proper radiation exposure level has been reached, the system 400 will notify the physician to remove the source wire, this alert can be audible via speaker 412 and/or visual using display 406.

The present invention allows physicians to get a quick understanding of the dosage levels that will be applied at different points of interest in a treatment site. The dosage information displayed at the different points of interest on an IVUS image allow the physician to adjust the treatment dosage in a quick and easy fashion, using well known point and click steps. Since the dosage table(s) 416 for different source wires 300 can be stored in the memory section 414 of system 400, an intravascular brachytherapy lab can use different radiation source wires and still take advantage of the present invention. The dosage tables 416 can be linked to different catheters either via manual entry as discussed above, or by automatically reading information stored in either the delivery catheter 100 or source wire 300. As discussed, the dosage tables can take into account the shielding effects of directional shields 102 found in some radiation delivery catheters, such as catheter 300.

Although the use of directional catheters is not required to practice all aspects of the present invention, they are beneficial to use given that most stenosis are typically non-centered with respect to the vessel lumen. Overall the present invention provides a simple and easy to use radiation treatment planning aid that can reduce the time physicians take per brachytherapy procedure. The dose table information is automatically updated by system 400 given the remaining half life of the source wire 300 at the time of use. The visual presentation of dose levels at selected point in IVUS image(s) coupled with the automatic dose table updating helps reduce the time it takes to formulate a treatment plan. The inclusion of on-screen markers helps the physician visualize the dosage levels at critical or important point of the stenosis. The displaying of the dosage levels at these selected points can help the physician adjust the treatment plan quickly by simply dragging the markers to different location in the image(s). Given this, the present invention can help reduce health care costs, and minimize the inconvenience to patients.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims.

What is claimed is:

1. A method for providing treatment planning for an intravascular ultrasound catheter guided radiation source, comprising the steps of:

positioning the intravascular ultrasound catheter in order to gain an image of a treatment site;

establishing a normalization point on the image having a specified radiation dosage level; and displaying said radiation dosage level along with the image.

2. A method as defined in claim 1, wherein the intravascular ultrasound catheter includes a radiation shield and further comprising the step of:

displaying at least one marker representing the position of the radiation shield.

3. A method as defined in claim 1, further comprising the step of:

using said normalization point to calculate the radiation dosage level at least at one other point on the image.

4. A method as defined in claim 3, further comprising the step of:

placing a marker on the image indicating the location of the at least one other point.

5. A method as defined in claim 1, further comprising the step of:

displaying a reference marker on the image which references the location of the normalization point on the image.

6. An intravascular ultrasound system for use in guiding a radiation source, comprising:

an ultrasound system;

a display coupled to the ultrasound system for displaying intravascular images;

a memory storage section coupled to the ultrasound system;

a radiation dosage table stored in the memory storage section, the radiation dosage table providing dosage rates relating to the radiation source; and a user interface coupled to the ultrasound system used for selecting a reference point on an intravascular ultrasound image and, in response, a reference marker and a dosage level for the reference marker are presented on the display along with the intravascular ultrasound image.

7. A intravascular ultrasound system as defined in claim 6, further comprising:

a directional radiation delivery catheter having a shield having a lumen for receiving the radiation source.

8. An intravascular ultrasound system as defined in claim 7 wherein the catheter comprises a memory, the memory having data which indicates a time and a date that the radiation source was created.

9. An intravascular ultrasound system as defined in claim 6, further comprising a notification mechanism for signaling that a radiation exposure level has been reached.

10. An intravascular ultrasound system as defined in claim 9, wherein the notification mechanism comprises a speaker.

11. An intravascular ultrasound system as defined in claim 9, wherein the notification mechanism comprises a visual display.

12. An intravascular ultrasound system as defined in claim 6 wherein the dosage rates provided by the radiation dosage table comprise empirical data.

13. An intravascular ultrasound system as defined in claim 6 wherein the dosage rates provided by the radiation dosage table comprise data generated from a simulation program.

* * * * *